(12) United States Patent
Callahan et al.

(10) Patent No.: US 11,986,620 B2
(45) Date of Patent: May 21, 2024

(54) FLUID-FITTING TOOL

(71) Applicant: CareFusion 303, Inc., San Diego, CA (US)

(72) Inventors: Ryan Callahan, Long Beach, CA (US); Wantjinarjo Suwito, West Linn, OR (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 17/946,983

(22) Filed: Sep. 16, 2022

(65) Prior Publication Data

US 2024/0091521 A1    Mar. 21, 2024

(51) Int. Cl.
*A61M 39/28* (2006.01)
*A61M 5/168* (2006.01)

(52) U.S. Cl.
CPC ........ *A61M 39/28* (2013.01); *A61M 5/16813* (2013.01)

(58) Field of Classification Search
CPC .... A61M 39/28; A61M 39/284; A61M 39/12; A61M 5/16813; A61M 2039/1077
USPC ....................................................... 251/9, 10
See application file for complete search history.

(56) References Cited

U.S. PATENT DOCUMENTS

| | | |
|---|---|---|
| 4,453,295 A | 6/1984 | Laszczower |
| 2005/0258382 A1* | 11/2005 | Yang ....................... F16K 7/063 251/7 |
| 2012/0232497 A1 | 9/2012 | Singh |
| 2017/0120038 A1 | 5/2017 | Tsukamoto et al. |
| 2017/0239443 A1* | 8/2017 | Abitabilo .......... A61M 25/0625 |
| 2018/0056043 A1* | 3/2018 | von Oepen ........... A61F 2/2427 |

OTHER PUBLICATIONS

International Search Report and Written Opinion for Application No. PCT/US2023/032209, dated Dec. 22, 2023, 11 pages.

* cited by examiner

*Primary Examiner* — Kelsey E Cary
(74) *Attorney, Agent, or Firm* — Morgan, Lewis & Bockius LLP

(57) ABSTRACT

A fluid-fitting tool is disclosed that can align with and rotationally couple with a fluid fitting where the fluid-fitting tool can include a passage and an engagement feature for engaging against the fluid fitting such that when the fluid-fitting tool is spaced apart from the fluid fitting, the fluid-fitting tool can move in a longitudinal direction toward and away from the fluid fitting, and can rotate relative to the fluid fitting around a longitudinal axis of the passage, and when a portion of the fluid-fitting tool and the fluid fitting are rotationally aligned and longitudinally overlap, the fluid-fitting tool can move longitudinally relative to the fluid fitting, and the fluid fitting is rotated when the fluid-fitting tool is rotated around a longitudinal axis of the passage.

18 Claims, 8 Drawing Sheets

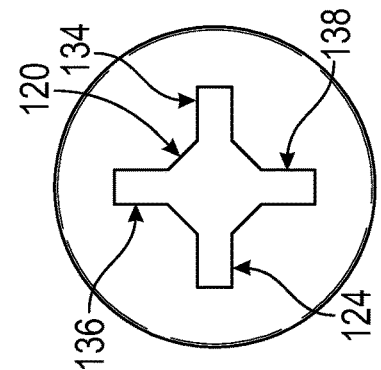
FIG. 8
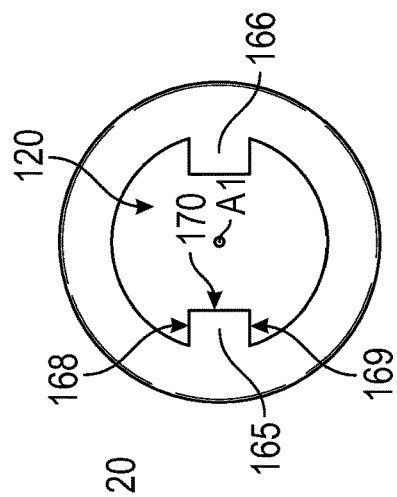
FIG. 12
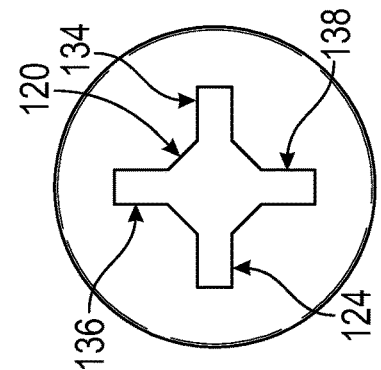
FIG. 7
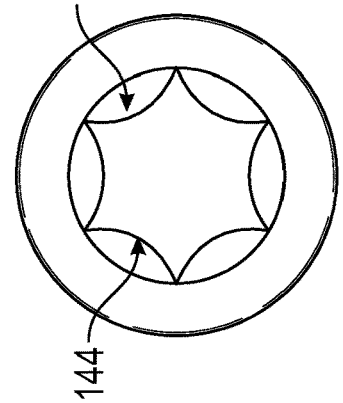
FIG. 11
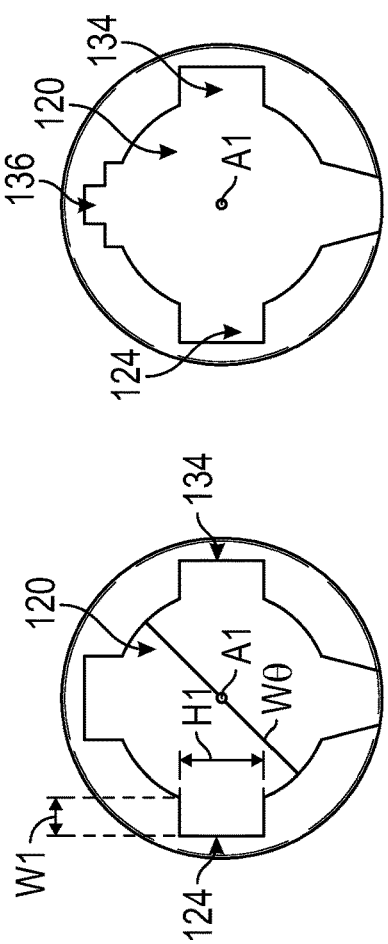
FIG. 6
FIG. 10
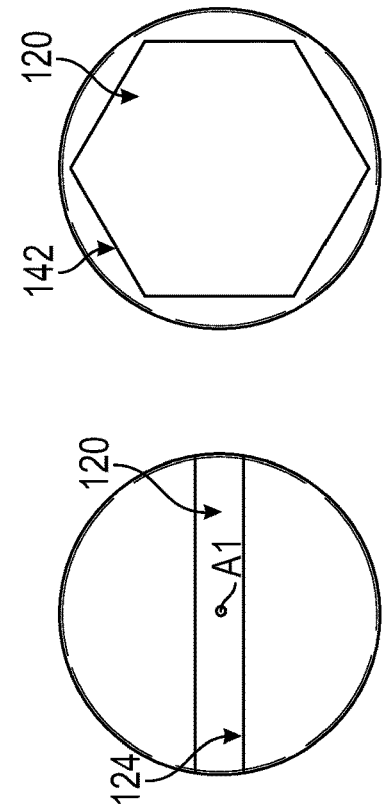
FIG. 9

FLUID-FITTING TOOL

BACKGROUND

The present disclosure relates generally to the movement of medical fluids, and more particularly, to devices and systems for connecting and disconnecting fluid fittings used for making leak-free connections in medical and laboratory instruments.

Medical procedures can require the intravenous (IV) administration of fluids such as a medicament via a gravity-fed IV bag, programmable pump, or injection. For example, liquid saline solution is commonly administered intravenously to patients who cannot take fluids orally or may have developed severe dehydration.

To administer a fluid and/or medicament intravenously, a catheter is often inserted into the patient's vein, the proximal end of which is connected to medical tubing. The medical tubing in turn is connected to a source of medical fluid, such as an IV bag. The combination of medical tubing, fitting, and connectors is commonly referred to as an "IV set."

The fitting between portions of the IV set, such as between the tubing and the catheter, can include a fluid fitting having a Luer taper, which is a standardized system of small-scale fluid fittings used for making leak-free connections between a male-taper fitting and its mating female part on medical and laboratory instruments.

An IV fluid administration can take place at periodic intervals over a length of time and patient treatment can require additional delivery of other therapeutic fluids. In some instances, the fluid fitting between portions of the IV set are disconnected to change the medicament, change the IV set, or to permit the patient to move without being coupled to the IV set.

In some instances, a disinfectant is applied to the fluid fittings to prevent contamination within the IV set, which can cause an infection of the patient when a fluid fitting between portions of the IV set are disconnected or changed. The application of a disinfectant can result in friction or adhesion between the fluid fittings, which can increase the resistance to disconnecting or unscrewing the fluid fittings. Similarly, factors such as the small cross-sectional width of the fluid fittings, placement of the fluid fittings proximal to the patient's body, and taping the catheter and/or a portion of the fluid fittings to the patient, can limit the ability to apply a torque to the fluid fittings and can cause disconnecting or unscrewing the fluid fittings to be difficult.

In some instances, the fluid fittings, tubing, catheter, or another portion of the medical fluid system is damaged if the fluid fittings are connected or disconnected using improper procedures or tools, such as the use of scissor, forceps, hemostats, or tourniquet rubber to apply torque to a fluid fitting for connection and disconnection thereof.

SUMMARY

In accordance with at least some embodiments disclosed herein is the realization that the use of improper procedures or tools for connecting or disconnecting fluid fittings can result in injury to a caregiver and a patient, damage to the fluid fitting or another portion of the fluid conveyance system. For example, a caregiver or the patient can incur an injury caused by use of an hemostat or other tool on a fluid fitting, a caregiver can incur fatigue and injury attempting to apply torque to a fluid fitting, and the patient can become infected if the fluid passage becomes contaminated. Additionally, the fluid fitting and other portions of the fluid conveyance system can become damaged by use of unintended tools and improper techniques for connecting or disconnecting a fluid fitting.

Accordingly, an aspect of the present disclosure provides a fluid-fitting tool for connecting or disconnecting a fluid fitting in a fluid conveyance system, such as an IV set or fluid conveyance system used in medical and laboratory instruments, while increasing efficiency, reducing potential injury to a caregiver or a patient, and avoiding damage the fluid fitting or another portion of the fluid conveyance system.

In some aspects of the present disclosure, fluid-fitting tools are disclosed comprising a body comprising a first end, a second end, an inner surface forming a passage that extends through the body between the first and second ends, and a first engagement feature comprising a first wall that extends from the inner surface of the passage and along a length that extends from the first end toward the second end of the body, wherein the passage is configured to receive at least a portion of a fluid fitting therein such that the first engagement feature engages an outer surface of the fluid fitting and rotationally couples the body and the fluid fitting such that, when the body is rotated around a longitudinal axis of the passage, the first engagement feature is configured to rotate the fluid fitting.

Some instances of the present disclosure provide fluid-fitting systems comprising a fluid fitting comprising: a proximal end portion, a distal end portion; an aperture that extends between the proximal and distal ends; and a tab that extends away from an outer surface of the fluid fitting, the tab positioned adjacent the proximal end, and a fluid-fitting tool comprising: a body comprising a first end, a second end, an inner surface forming a passage that extends through the body between the first and second ends, and a first engagement feature comprising a first wall that extends from the inner surface of the passage, wherein the fluid-fitting tool comprises: a first configuration in which the fluid-fitting tool is spaced apart from the fluid fitting such that the fluid-fitting tool is rotatable relative to the fluid fitting; and a second configuration, in which at least a portion of a fluid fitting is positioned within the fluid-fitting tool such that when the body is rotated around a longitudinal axis of the passage, the first engagement feature engages against the tab such that the fluid fitting rotates with the body.

The present disclosure also provides methods of separating a fluid fitting comprising positioning a tubing through a passage of a fluid-fitting tool, moving the fluid-fitting tool, in a longitudinal direction along a length of the tubing, toward a fluid fitting such that a tab of the fluid fitting is at least partially positioned within the passage, and rotating the fluid-fitting tool around a longitudinal axis of the passage and relative to the fluid fitting, to engage a first wall of the fluid-fitting tool against the tab of the fluid fitting such that the fluid fitting rotates with the fluid-fitting tool.

Accordingly, the present application addresses several operational challenges encountered in prior fluid fitting connections and provides numerous improvements that enable the user to more easily and precisely connect and disconnect fluid fittings.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIGS. 6-12 illustrate detail views of profiles for passages and engagement features of fluid-fitting tools, in accordance with aspects of the present disclosure.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present application discloses various features and advantages of a fluid-fitting tool. The fluid-fitting tool can provide for more efficient and safe connection and disconnection of fluid fittings by increasing the potential torque that can be applied to the fluid fitting. The present disclosure also minimizes potential injury to a caregiver or a patient during connecting or disconnecting a fluid fitting, and minimizes potential damage to a fluid fitting or another portion of the fluid conveyance system. For example, the fluid-fitting tool can provide a solution for safe and efficient connecting or disconnecting a fluid fitting relative to connecting or disconnecting the fluid fitting by directly grasping the fluid fitting with a hand or using a tool that is not intended for use with a fluid fitting.

Figure 1:
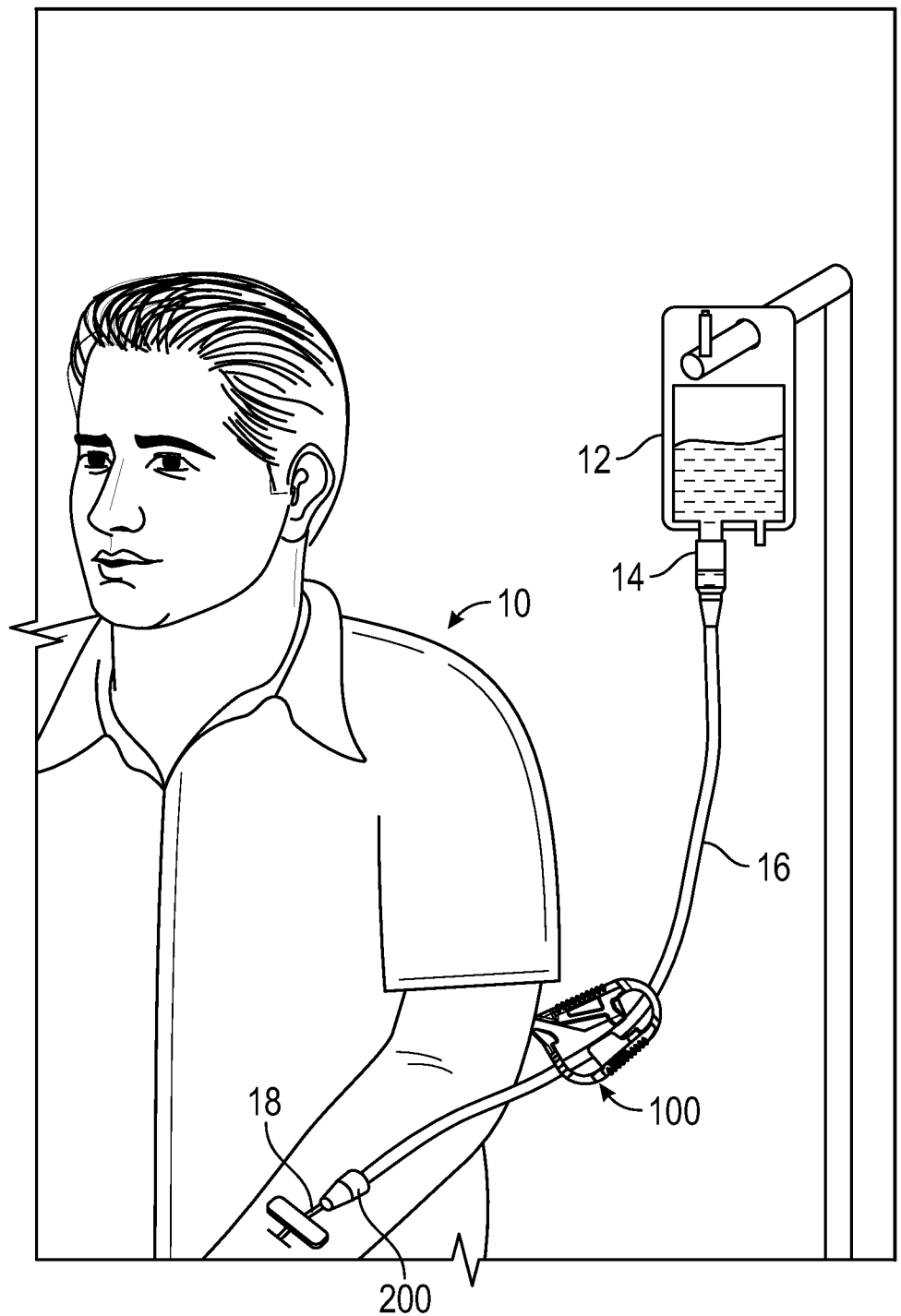
FIG. 1 illustrates a fluid-fitting tool in use with an IV set coupled to a patient, in accordance with aspects of the present disclosure.

Referring now to the figures, FIG. 1 illustrates an example of a fluid-fitting tool 100 in use in accordance with aspects of the present disclosure. The fluid-fitting tool 100 is coupled with tubing of an IV set, which being used to deliver a fluid to a patient 10. The IV set includes a medicament bag 12, a drip chamber 14, tubing 16, an IV catheter 18, and a fluid fitting 200.

The fluid fitting 200 fluidly connects the tubing 16 to the IV catheter 18. To disconnect the IV set from the patient 10, the fluid fitting 200 can be separated from the IV catheter 18. In some instances, the fluid fitting 200 is separated from the IV catheter 18 to permit intravenous injection of a medicament directly into the patient through the catheter 18.

In use, the fluid fitting 200 can be connected to the IV catheter 18 by threaded surface therebetween, a twist-lock structure of the fluid fitting 200 and/or catheter 18, an interference-fit connection between the fluid fitting 200 and catheter 18, or other structure. In some instances, a disinfectant may be applied to any of the surfaces of the fluid fitting 200 and the IV catheter 18 to prevent infection of the patient.

The fluid-fitting tool 100 is coupled to the tubing 16, between the drip chamber 14 and the fluid fitting 200. To couple the fluid-fitting tool 100 to the tubing, a length of the tubing can be inserted through a passage of the fluid-fitting tool 100 before the IV set is coupled to the patient. In some aspects of the present disclosure, the fluid-fitting tool 100 can be coupled to the tubing after the IV set is coupled to the patient, such as by laterally inserting the tubing 16 into a passage of the fluid-fitting tool 100.

Figure 2:
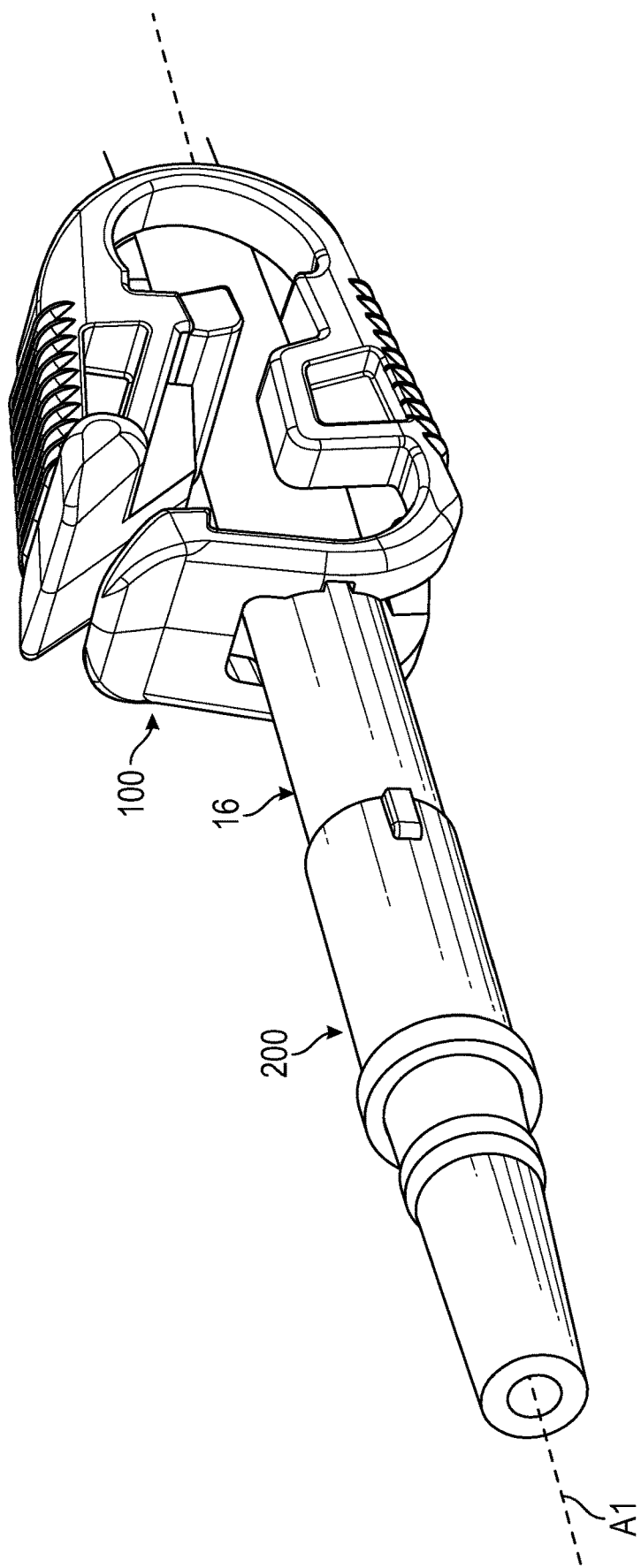
FIG. 2 illustrates a perspective view of a fluid-fitting tool coupled to a length tubing and spaced apart from a fluid fitting, in accordance with aspects of the present disclosure.

The fluid-fitting tool 100 can be coupled to the tubing 16 and positioned to be spaced apart from the fluid fitting 200, as illustrated in FIG. 2. When coupled to the tubing, a portion of the tubing 16 extends through a passage of the fluid-fitting tool 100 to the fluid fitting 200. When the fluid-fitting tool 100 is coupled to the tubing 16 and spaced apart from the fluid fitting 200, the fluid-fitting tool 100 can be moved along the tubing 16 in a direction toward or away from the fluid fitting 200. In some aspects of the present disclosure, the fluid-fitting tool 100 can be rotated around the tubing when the fluid-fitting tool 100 is spaced apart from the fluid fitting 200.

Figure 3:
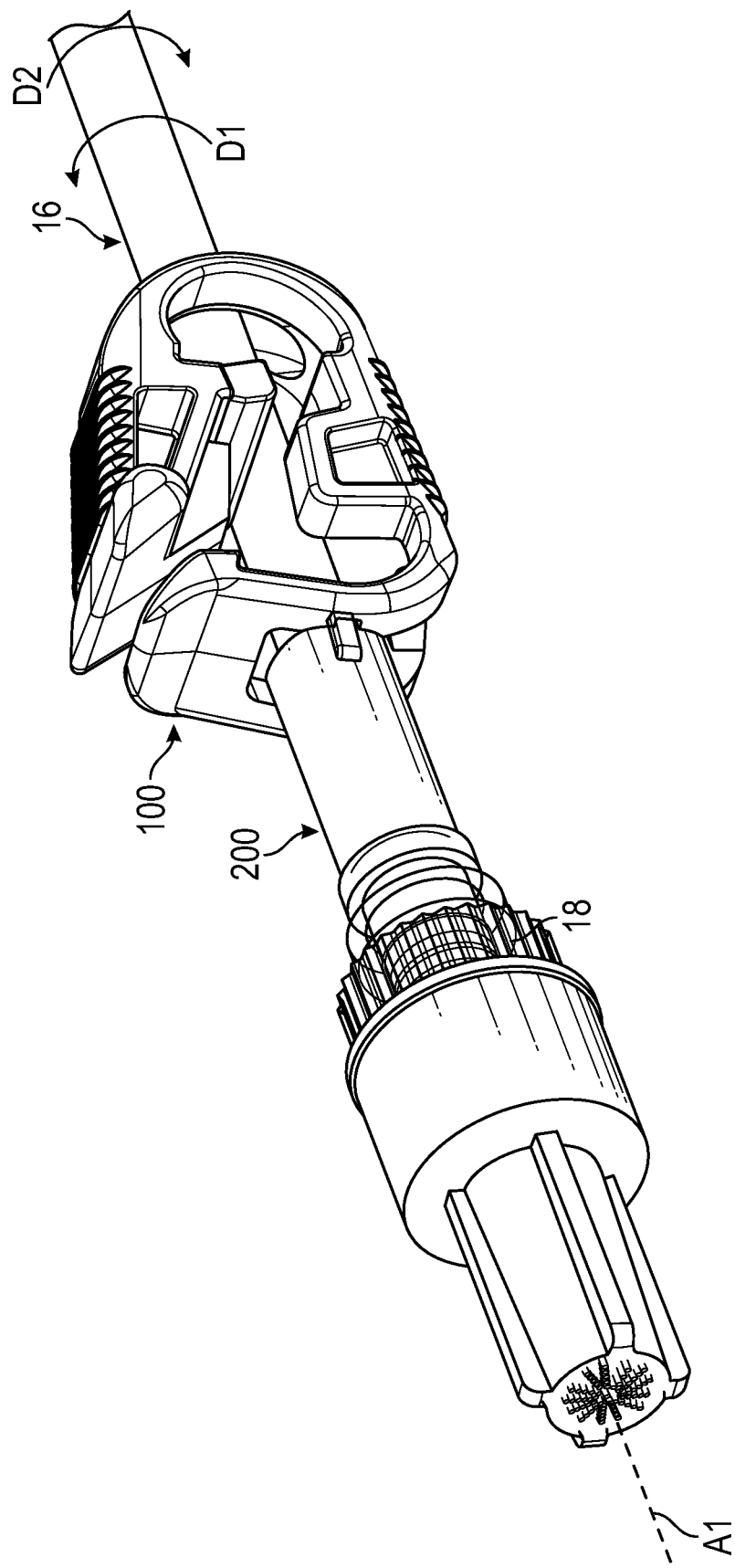
FIG. 3 illustrates a perspective view of a fluid-fitting tool coupled to a length tubing and engaged against a fluid fitting, in accordance with aspects of the present disclosure.

To connect or disconnect the fluid fitting 200 with another device, the fluid-fitting tool 100 can be moved along the tubing 16 in a direction toward the fluid fitting 200 until the fluid-fitting tool 100 engages against the fluid fitting 200. In some embodiments of the present disclosure, the fluid-fitting tool 100 is moved until a portion of the fluid fitting 200 is positioned within the fluid-fitting tool 100, as illustrated in FIG. 3. In some aspects of the present disclosure, the fluid-fitting tool 100 and/or the fluid fitting 200 are moved toward each other until at least a portion of the fluid-fitting tool 100 or the fluid fitting 200 overlaps with the other of the fluid-fitting tool 100 or the fluid fitting 200.

FIG. 3 illustrates the fluid-fitting tool 100 and fluid fitting 200 positioned with a proximal portion of the fluid fitting 200 within a passage of the fluid-fitting tool 100. To permit the proximal portion of the fluid fitting 200 to be inserted into the passage of the fluid-fitting tool 100, the fluid-fitting tool 100 can be rotated in a first direction D1 or second direction D2 around the tubing 16 until an engagement feature of the fluid-fitting tool 100 is aligned with a complementary feature of the fluid fitting 200. The complementary feature of the fluid fitting 200 can include any of a tab, protrusion, pin, ledge, pin, convex surface, concave surface, groove, notch, channel, or structure.

When the fluid-fitting tool 100 is positioned with the engagement feature of the fluid-fitting tool rotationally and longitudinally aligned with the complementary feature of the fluid fitting 200, rotation of the fluid-fitting tool 100 around a longitudinal axis A1 of the passage and relative to the fluid fitting 200, can engage the engagement feature of the fluid-fitting tool 100 against the complementary feature of the fluid fitting 200. In some embodiments of the present disclosure, the engagement feature of the fluid-fitting tool 100 engages against an outer surface of the fluid fitting 200.

When the fluid-fitting tool 100 is rotated with the engagement feature rotationally and longitudinally aligned with the complementary feature of the fluid fitting 200, the fluid-fitting tool 100 and the fluid fitting 200 become rotationally coupled such that they can rotate together around the a common axis, such as the longitudinal axis A1.

In some aspects of the present disclosure, the rotationally coupled fluid-fitting tool 100 and fluid fitting 200 can be rotated in the first direction D1 to connect the fluid fitting 200 to a catheter 18 or another device, and the rotationally coupled fluid-fitting tool 100 and fluid fitting 200 can be rotated in the second direction D2 to disconnect the fluid fitting 200 from the catheter 18 or other device, where the second direction D2 is opposite to the first direction D1.

It should be understood that, although the fluid-fitting tool 100 and fluid fitting 200 are illustrated with features of an IV set, the features of the present disclosure can be used with other fluid conveyance systems, equipment, instruments, and/or devices.

Figure 4:
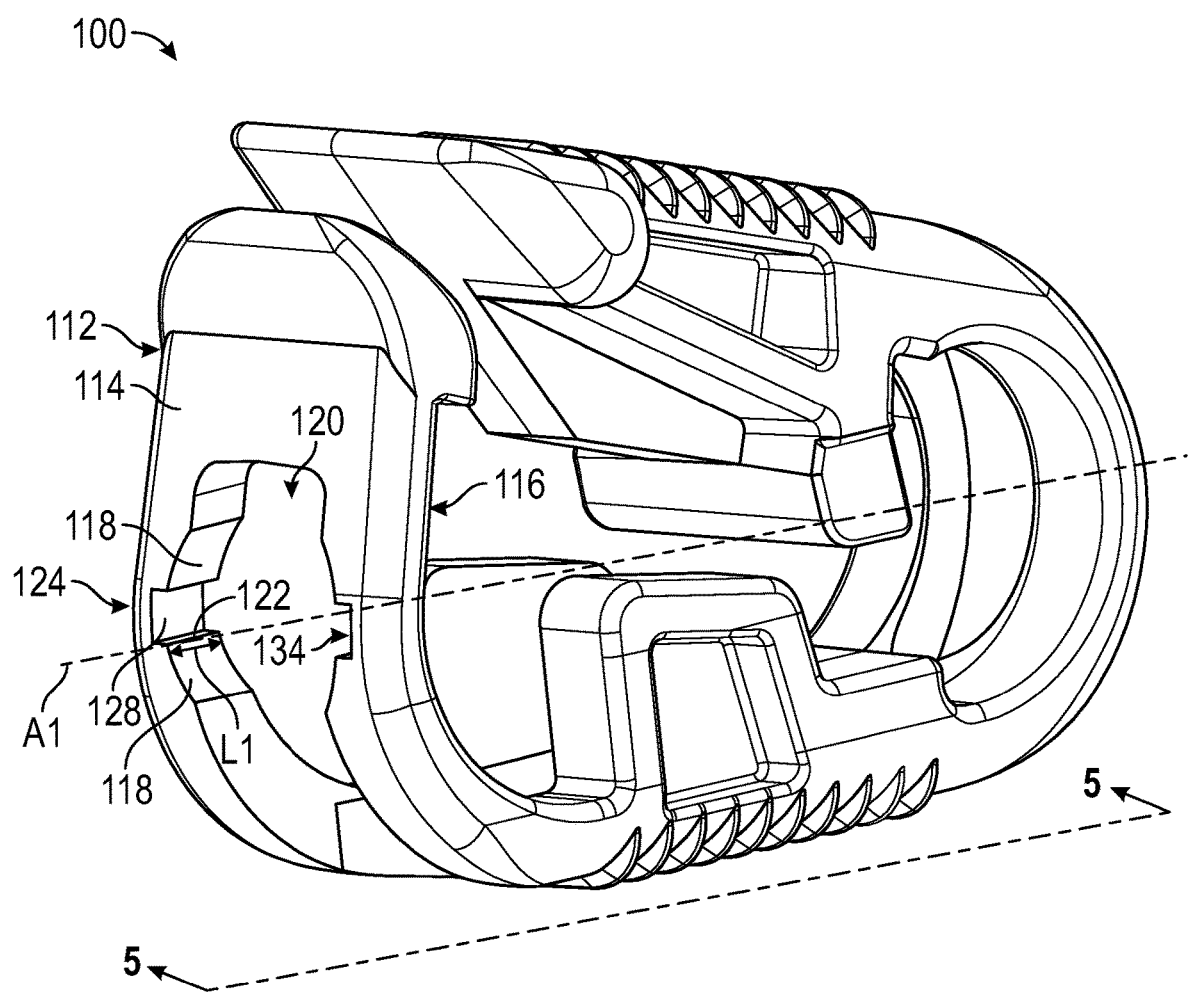
FIG. 4 illustrates a perspective view of a fluid-fitting tool, in accordance with aspects of the present disclosure.

Referring to FIG. 4, a fluid-fitting tool 100 is illustrated. The fluid-fitting tool 100 can have a body 112 with a first end 114, a second end 116, and an inner surface 118 forming a passage 120 that extends through the body 112 between the first and second ends 114, 116.

The passage 120 defines a longitudinal axis A1 that extends through the passage 120, between the first and second ends. The passage 120 defines a cross-sectional profile, transverse relative to the longitudinal axis of the passage, defining a passage area and having a width W0 (FIG. 6). The width W0 of the passage can be equal to or greater than a width of the tubing 16. The cross-sectional profile is configured with a size and/or shape to permit the tubing 16 to be inserted therethrough.

The fluid-fitting tool 100 includes a first engagement feature 124 having a first wall 122 that extends from the inner surface 118 of the passage and is configured to engage against a fluid fitting. The first wall 122 extends along a length L1, from the first end 114 toward the second end 116 of the body. The length L1 of the first wall 122 is oriented in a direction that is approximately parallel to the direction of the longitudinal axis A1 through the passage. In some embodiments, the length L1 of the first wall 122 extends from the first end 114 to the second end 116 of the body.

The first wall 122 extends from the inner surface 118 of the passage in a direction away from the passage 120 to define a width W1. Because the first wall 122 extends along a width W1 from the inner surface 118 of the passage in a direction away from the passage 120, a width of the passage 120 at the first engagement feature 124 is greater than a width of the passage 120 at a portion adjacent to the first wall 122. As such, the area defined by passage the cross-sectional profile of the passage is greater than an are defined by the cross-sectional profile defined by the channel. The larger width of the passage at the first engagement feature 124 can permit insertion of complementary feature of a fluid fitting 200, such as a protrusion or tab.

Figure 5:
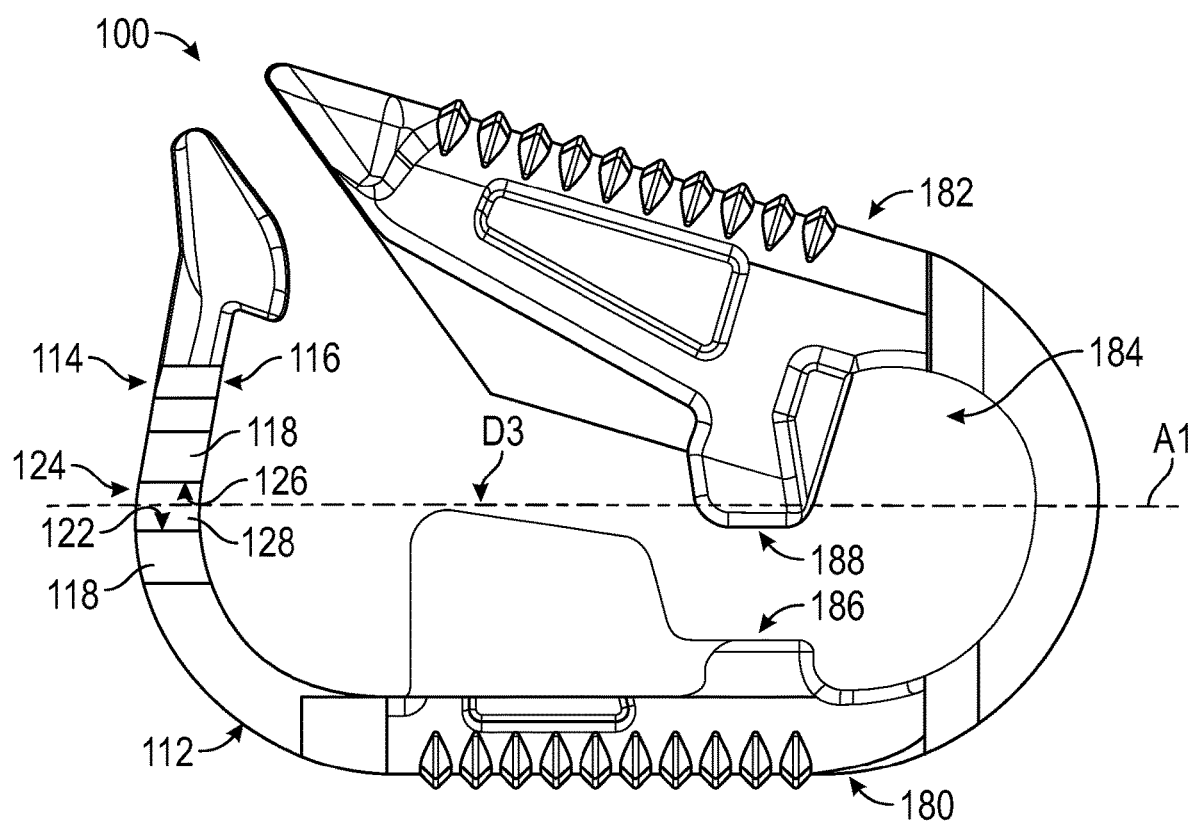
FIG. 5 illustrates a cross-sectional elevation view of the fluid-fitting tool of FIG. 4, in accordance with aspects of the present disclosure.

The first engagement feature 124 is shaped as a channel having the first wall 122 and a second wall 126, as shown, for example, in FIGS. 4 and 5, where FIG. 5 illustrates a cross-sectional view of FIG. 4 along the line 5-5. The first and second walls 122, 126 extend from the inner surface 118 of the passage in a direction away from the longitudinal axis A1 to form at least a portion of the first engagement feature 124. To form the first engagement feature 124, the first and second walls 122, 126 can intersect each other to define the channel of the first engagement feature 124.

In some aspects of the present disclosure, a third wall 128 extends between the first and second walls 122 and 126 to define the channel of the first engagement feature 124. In some embodiments of the present disclosure, the channel can have a cross-sectional profile that is transverse relative to the longitudinal axis A1, where the cross-sectional profile of the channel forms any of a concave shape, a U-shaped, a V-shape, or the like.

In some embodiments of the present disclosure, the fluid-fitting tool 100 can include a second engagement feature 134 configured to permit insertion of another complementary feature of a fluid fitting 200, such as another protrusion or tab. The second engagement feature 134 can provide additional surface area for engagement against a fluid fitting, thereby permitting a greater application of torque against the fluid fitting relative to a fluid-fitting tool 100 having a single engagement feature.

The second engagement feature 134 can include the same or similar features as the first engagement feature 124, including, but not limited to, a first wall, a second wall, and a third wall. However, it should be understood that the first and second engagement features 124, 134 can have any of the same shape and size, or the first and second engagement features 124, 134 can each have a different shape and/or size.

In some embodiments of the present disclosure, the fluid-fitting tool 100 can comprise one or more engagement features having different shapes and orientations. For example, FIGS. 6-12 illustrate cross-sectional profiles for fluid-fitting tools having engagement feature with various shapes and orientations.

FIG. 6 illustrates a cross-sectional profile of a passage 120 of a fluid-fitting tool with first and second engagement features 124 and 134. The first engagement feature 124 and the second engagement feature 134 are spaced apart approximately opposite relative to each other around the longitudinal axis A1 of the passage. In some embodiments, the first and second engagement features 124 and 134 are spaced apart around the longitudinal axis A1 of the passage between about 1 and 180 degrees. In some aspects of the present disclosure, the first and second engagement features 124 and 134 are spaced apart around the longitudinal axis A1 of the passage between about 45 and 135 degrees. In some examples, the first and second engagement features 124 and 134 are spaced apart around the longitudinal axis A1 of the passage about 90 degrees.

FIG. 7 illustrates a cross-sectional profile of a passage 120 with a first engagement feature 124, a second engagement feature 134, and a third engagement feature 136. The third engagement feature 136 is positioned between the first and second engagement features 124 and 134. In some embodiments, the first, second, and third engagement features 124, 134, 136 are equally spaced apart around the longitudinal axis A1 of the passage. In some aspects of the present disclosure, the first, second, and third engagement features 124, 134, 136 can be spaced apart around the longitudinal axis A1 of the passage by different distances.

Referring to FIG. 8, a cross-sectional profile of a passage 120 is illustrated having a first engagement feature 124, a second engagement feature 134, a third engagement feature 136, and a fourth engagement feature 138. Each of the first, second, third, and fourth engagement features 124, 134, 136, 138 can be equally spaced apart around the axis A1. In some embodiments, the first, second, third, and fourth engagement features 124, 134, 136, 138 can be spaced apart around the longitudinal axis A1 of the passage by different distances.

FIG. 9 illustrates a cross-sectional profile of a passage 120 having a slot shape formed by a first engagement feature 124, where the first engagement feature 124 has a width that extends in opposite directions that are transverse relative to the axis A1.

FIG. 10 illustrates a cross-sectional profile of a passage 120 having an engagement feature 142 formed by a plurality of walls. Each of the walls can have a width that extends in a direction transverse relative to the axis A1. The width of the walls can extend in a straight direction and intersect two adjacent walls. In some aspects of the present disclosure, six walls are spaced apart by about the same angle to form a hexagonal shape. In some embodiments, an engagement feature 144 is formed by an inner surface of the passage having a plurality of walls with a convex shape, as illustrated in the cross-sectional profile of a passage 120 of FIG. 11. Each of the walls have a width that extends in a curved direction away from the axis A1.

FIG. 12 illustrates a cross-sectional profile of a passage 120 having an engagement feature 165 formed, at least in part, by a wall that extends from an inner surface of the passage toward the longitudinal axis A1. The engagement feature 166 can be formed by first and second walls 168, 169 that extend into the passage, and a third wall 170 that extends between the first and second walls 168, 169. In some embodiments, first and second engagement features 165, 166 can extend into the passage and toward the longitudinal axis A1. The first and second engagement features 165, 166 can be configured to extend into a channel of a fluid fitting when the fluid fitting and fluid-fitting tool 100 are moved toward each other.

In some embodiments of the of the present disclosure, such as the embodiments illustrated in FIGS. 4 and 5, the fluid-fitting tool 100 can be configured to clamp or compress a length of tubing 16.

To compress a length of tubing, the fluid-fitting tool 100 includes include a first arm 180 and a second arm 182 that can engage against a length tubing extending within the fluid-fitting tool. The first and second arms 180 and 182 have an inner surface forming a cavity 184 that is continuous with the passage 120 so that the longitudinal axis A1 of the passage extends through the cavity 184. In use, a length of tubing can be inserted through the passage 120 and the cavity 184 to extend entirely through the fluid-fitting tool 100.

The first arm 180 extends away from the body 112, and the second arm 182 extends from the first arm 180, toward the body 112. Any of the first and second arms 180 and 182 are moveable, relative to each other and the body 112, to increase or decrease the distance between the inner surfaces of the first and second arms 180 and 182.

The second arm 182 can be moveable between first and second positions. In the first position, the inner surface 188 of the second arm is positioned along the cavity 184 to define a first cross-sectional clearance between the inner surface 188 of the second arm and the inner surface 186 of the first arm. In the second position, the second arm 182 is moved in a direction D3 toward the first arm 180 to define a second cross-sectional clearance between the inner surface 188 of the second arm and the inner surface 186 of the first arm, where the second cross-sectional clearance is less than the first cross-sectional clearance.

In some aspects of the present disclosure, when the second arm 182 is in the second position, at least a portion of the second arm 182 extends into the cavity 184 to change a cross-sectional profile of the cavity 184 relative to when the second arm 182 is in the first position. In some embodiments of the present disclosure, each of the first and second arms 180, 182, extend away from the body, and any of the first and second arms 180, 182 can be moveable in a direction toward the other of the first and second arms 180, 182.

Figure 13:
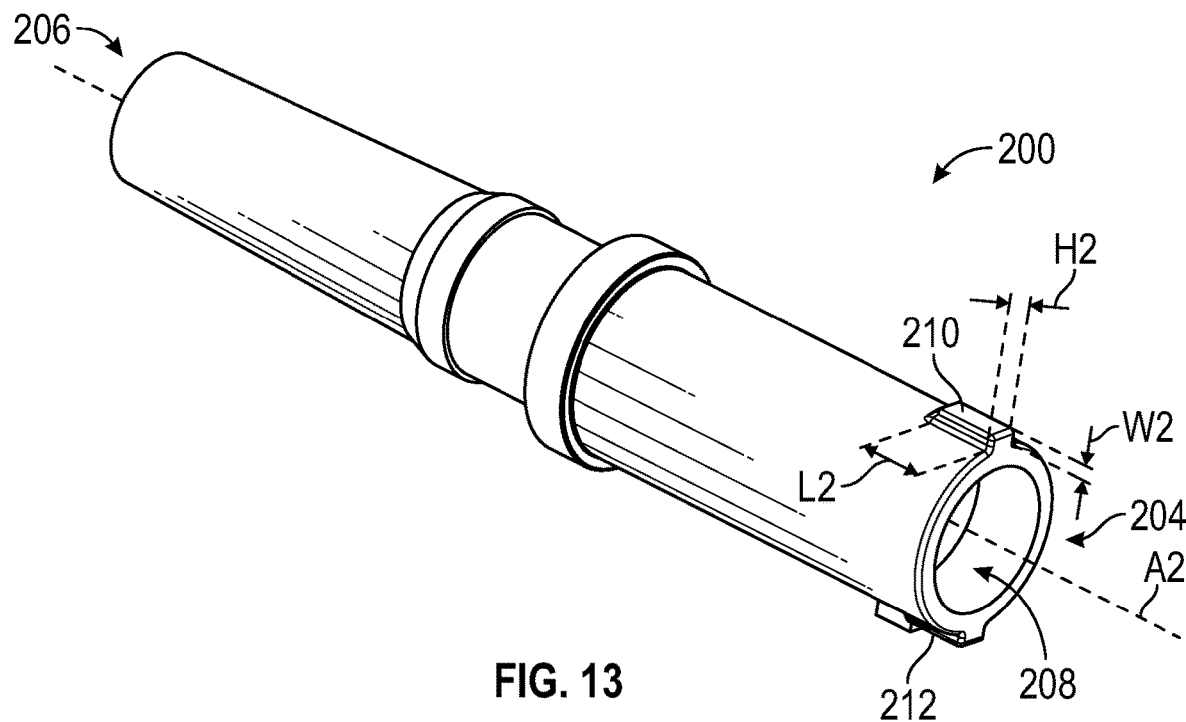
FIG. 13 illustrates a perspective view of a fluid fitting, in accordance with aspects of the present disclosure.

An embodiment of a fluid fitting is illustrated in FIG. 13. The fluid fitting 200, or a portion thereof, is configured to be received into the passage of the fluid-fitting tool 100 so that, when the fluid-fitting tool 100 is rotated relative to the fluid fitting 200, the fluid fitting 200 and fluid-fitting tool 100 become rotationally coupled. Although embodiments of fluid fittings are described in the present disclosure, it should be understood that the fluid-fitting tool 100 can be used with other fluid fittings and connector such that the fluid-fitting tool 100 can engage against and be rotationally coupled with the fluid fitting.

The fluid fitting 200 can include a proximal end portion 204, a distal end portion 206, and an aperture 208 that extends between the proximal and distal end portions 204 and 206. An end portion of the fluid fitting, such as the proximal end portion 204, can be connected with a length of tubing so that the aperture 208 is fluidly coupled with the tubing.

The fluid fitting 200 comprises a tab 210 that extends away from an outer surface of the fluid fitting and is configured to engage against the engagement feature of the fluid-fitting tool 100. In some aspects of the present disclosure, the tab 210 is configured so that the fluid-fitting tool 100 can move relative to the fluid fitting 200, and independent of the fluid fitting 200, along the longitudinal axis A2 of the fluid fitting. However, when the fluid-fitting tool 100 is rotated around the longitudinal axis A2, the engagement feature of the fluid-fitting tool 100 engages against the tab 210 to rotationally couple the fluid-fitting tool 100 and fluid fitting 200.

The tab 210 is positioned along the proximal end portion 204 of the fluid fitting so that the engagement feature of the fluid-fitting tool 100 can engage against the tab 210 when the proximal end portion 204 of the fluid fitting is positioned within the passage of the fluid-fitting tool 100. The tab 210 comprises a width W2 that extends radially outward from the outer surface of the fluid fitting in a direction away from the longitudinal axis A2. The tab 210 also comprises a length L2 that extends along the outer surface of the fluid fitting, in a direction from the proximal end portion 204 toward the distal end portion 206 of the fluid fitting. Further, the tab 210 comprises a height H2 that extends along the outer surface of the fluid fitting, in a direction that is transverse relative to the direction of the width W2 and length L2 of the tab. The width W2 and height H2 of the tab are approximately equal to or less than the width W1 and height H1 of the engagement feature of the fluid-fitting tool 100.

In some embodiments, the fluid fitting comprises a second tab 212, such that the first and second tabs 210, 212 are each configured to align with and be received into first and second engagement features 124, 134 of the fluid-fitting tool, respectively.

Any of the first and second tabs 210, 212 can be positioned along the proximal and/or distal end portions of the fluid fitting 200, and the fluid-fitting tool 100 and fluid fitting 200 can be moved toward each other until the first and second tabs 210, 212 are longitudinally aligned with the engagement feature of the fluid-fitting tool 100.

In some embodiments of the present disclosure, the engagement features and tabs can be configured to require rotational alignment of the fluid-fitting tool 100, relative to the fluid fitting, before the fluid-fitting tool 100 can be rotationally coupled with the fluid fitting. For example, the fluid-fitting tool 100 may need to be rotated until the first engagement feature 124 is rotationally aligned with the first tab 210, and the second engagement feature 134 is rotationally aligned with the second tab 212, before the fluid fitting 200 can be received into the passage.

To require rotational alignment of the fluid-fitting tool 100 and the fluid fitting, the first engagement feature 124 can have a width W1 and/or height H1 that is different than a width and/or height of the second engagement feature 134, and the first tab 210 can have width W2 and/or height H2 that is different than a width and/or height of the second tab 212. As such, any of the fluid-fitting tool 100 and the fluid fitting could resist coupling therebetween without aligning an engagement feature 124, 134 with a complementary first and second tab 210, 212.

Figure 14:
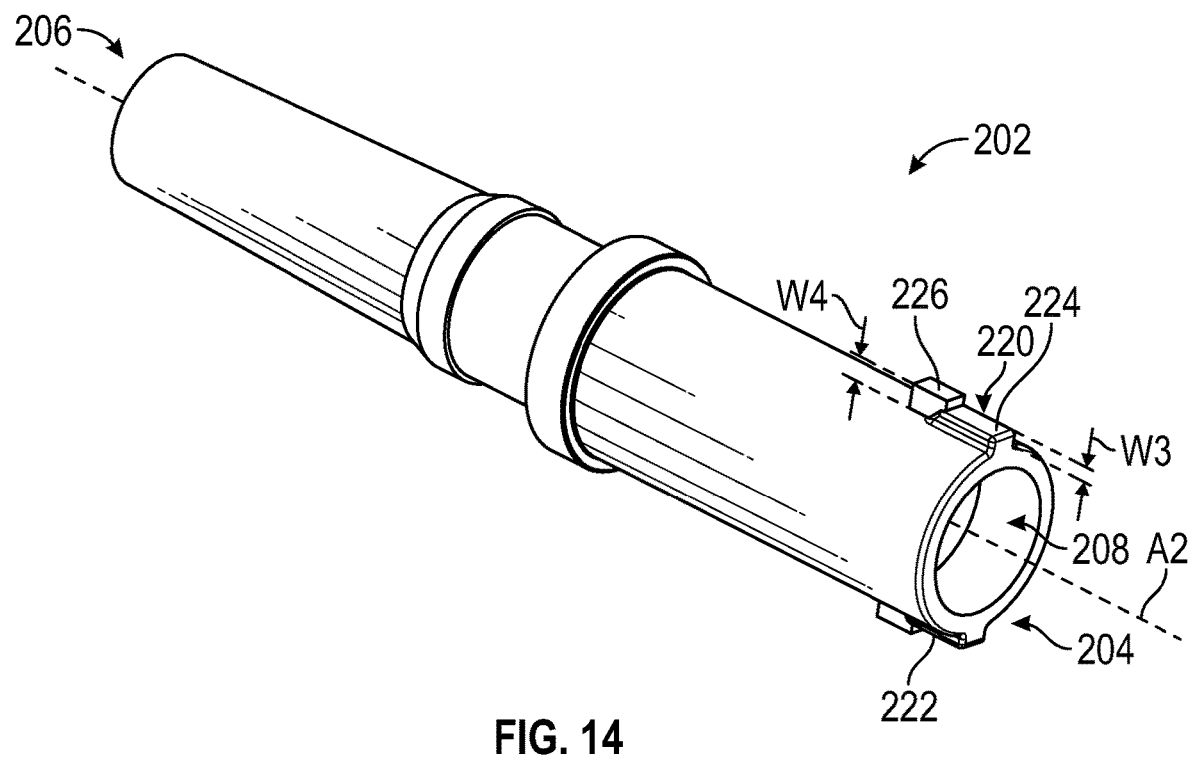
FIG. 14 illustrates a perspective view of another embodiment of a fluid fitting, in accordance with aspects of the present disclosure.

Referring to FIG. 14, an embodiment of a fluid fitting 202 is illustrated having a movement-limiting feature, which can resist unintended movement of the fluid-fitting tool 100 toward the distal end of the fluid fitting 202. Other features of the fluid fitting 202, which are similar or the same as features shown and described with reference to the fluid fitting 200, are described with like reference numbers herein for clarity and brevity.

To resist unintended movement of the fluid-fitting tool 100 toward the distal end portion 206 of the fluid fitting, a protrusion can extend from the outer surface of the fluid fitting. The protrusion can be formed by a tab 220 of the fluid fitting 202 having a first portion 224 with a first width W3, and a second portion 226 with a second width W4, where the second width W4 is greater than the first width. In some aspects of the present disclosure the fluid fitting 202 can comprise more than one tab, such as a second tab 222, that is spaced apart from the first tab 220.

The first width W3 is approximately equal to or less than the width W1 of the engagement feature of the fluid-fitting tool 100. In use, the fluid-fitting tool 100 and the fluid fitting 202 can be moved toward each other until the first portion 224 is positioned within the an engagement feature of the fluid-fitting tool 100. Upon further movement of the fluid-fitting tool 100 and the fluid fitting 202 toward each other, the fluid-fitting tool 100 could engage against the second portion 226 of the tab 220, thereby resisting further movement of the fluid-fitting tool 100 toward the distal end portion 206 of the fluid fitting.

In some embodiments of the present disclosure, the longitudinal movement-limiting feature can be formed by a protrusion that is spaced apart from the tabs 220, 222. As such, when the tabs 220, 222, are positioned within the engagement features of the fluid-fitting tool, further longitudinal movement of the fluid-fitting tool along the fluid fitting 202 can be resisted by engagement of the fluid-fitting tool against the longitudinal movement-limiting feature.

In some embodiments of the present disclosure, any of the engagement feature of the fluid-fitting tool 100 and the tab of the fluid fitting 200 can have a width that tapers to resist longitudinal movement therebetween. In some embodiments, the width W1 of the first wall of the engagement feature tapers or decreases in a direction away from the first end 114 of the fluid-fitting, and a width W2 of the tab increases in a direction away from the proximal end portion 204 of the fluid fitting.

Figure 15:
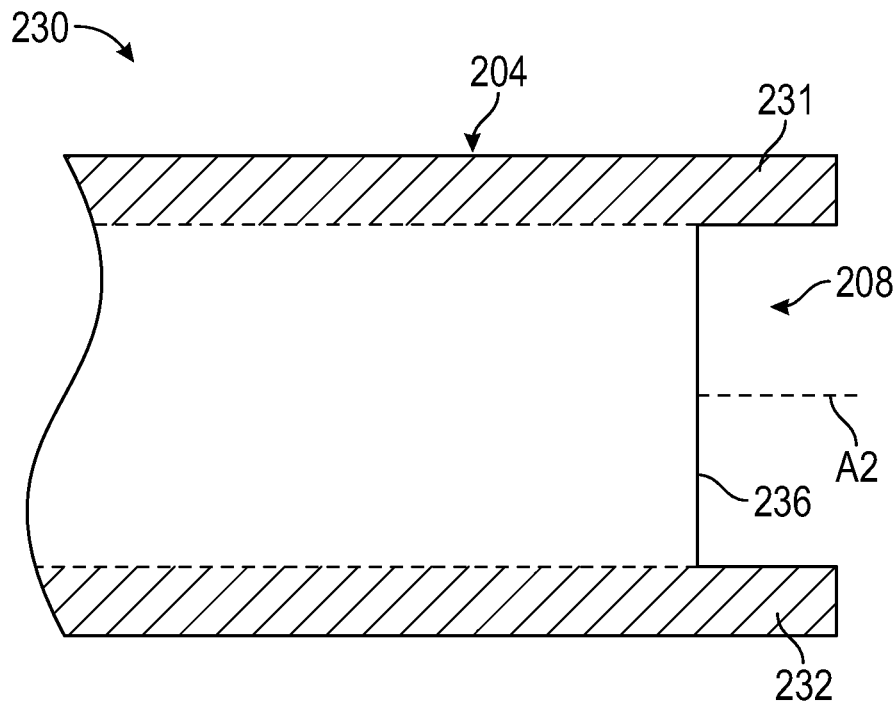
FIG. 15 illustrates a cross-sectional detail view of another embodiment of a fluid fitting, in accordance with aspects of the present disclosure.

Referring to FIG. 15, a proximal end portion 204 of an embodiment of a fluid fitting 230 is illustrated in a cross-sectional view. The fluid fitting 230 can have a tab that extends from an end of the fluid fitting. The proximal end portion can include a proximal end 236, a first tab 231, and a second tab 232. The first and second tabs 231, 232 extend from the proximal end 236 of the fluid fitting, in a direction that is away from the distal end of the fluid fitting. In some aspects of the present disclosure, the first and second tabs 231, 232 extend in a direction that is away from the distal end of the fluid fitting and is approximately parallel to a longitudinal axis A2 of the fluid fitting.

In use, the fluid-fitting tool 100 and the fluid fitting can be moved toward each other until a tab 231, 232 is positioned within an engagement feature of the fluid-fitting tool 100. Upon rotation of the fluid-fitting tool 100 around the longitudinal axis A1, the engagement feature of the fluid-fitting tool 100 engages against the tab 231, 232 to rotationally couple the fluid-fitting tool 100 and fluid fitting.

Figure 16:
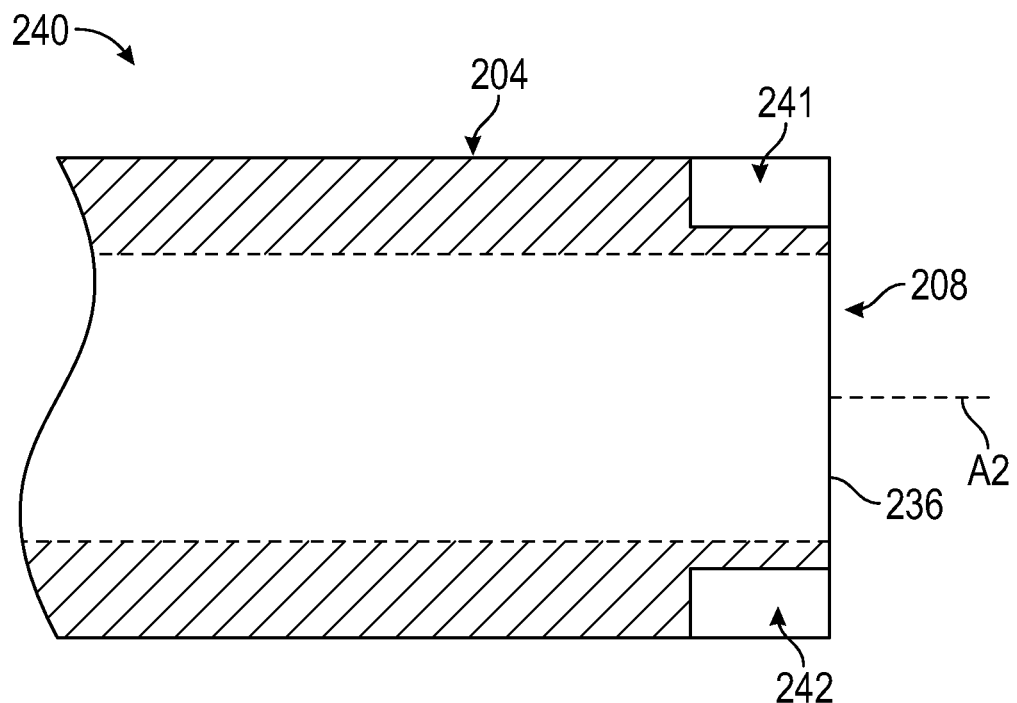
FIG. 16 illustrates a cross-sectional detail view of another embodiment of a fluid fitting, in accordance with aspects of the present disclosure.

Referring to FIG. 16, a proximal end portion 204 of a fluid fitting 240 is illustrated in a cross-sectional view. The fluid fitting 240 can have a notch that extends into an outer surface of the fluid fitting toward the longitudinal axis A2. The proximal end portion 204 includes a proximal end 236, a first notch 241, and a second notch 242. The first and second notches 241, 242 extend in a direction that is away from the proximal end 236 of the fluid fitting and is approximately parallel to a longitudinal axis A2 of the fluid fitting.

Each of the first and second notches 241, 242 extend around a portion of the circumference defined by the outer surface of the fluid fitting 240. In use, the fluid-fitting tool can be rotated until a tab of the fluid-fitting tool is aligned with any of the first and second notches 241, 242. Upon alignment of the tab of the fluid-fitting tool with the notch of the fluid fitting, the fluid-fitting tool can be further moved along the fluid fitting to rotationally couple the tab of the fluid-fitting tool with the notch of the fluid fitting.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A fluid-fitting tool comprising a body comprising a first end, a second end, an inner surface forming a passage that extends through the body between the first and second ends, and a first engagement feature comprising a first wall that extends from the inner surface of the passage and along a length that extends from the first end toward the second end of the body; wherein the passage is configured to receive at least a portion of a fluid fitting therein such that the first engagement feature engages an outer surface of the fluid fitting and rotationally couples the body and the fluid fitting such that, when the body is rotated around a longitudinal axis of the passage, the first engagement feature is configured to rotate the fluid fitting.

Clause 2. The fluid-fitting tool of Clause 1, wherein the first wall extends from the first end to the second end of the body in a first direction, the passage extends from the first end to the second end of the body in a second direction, and the first and second directions are parallel relative to each other.

Clause 3. The fluid-fitting tool of any of Clauses 1 and 2, wherein the first wall extends from the inner surface in a direction away from the passage.

Clause 4. The fluid-fitting tool of any of Clauses 1 to 3, wherein the first wall extends from the inner surface in a direction toward the passage.

Clause 5. The fluid-fitting tool of Clause 4, further comprising a second wall that extends from the inner surface of the passage and intersects with the first wall.

Clause 6. The fluid-fitting tool of Clause 5, wherein the first and second walls form a channel of the engagement feature.

Clause 7. The fluid-fitting tool of Clause 6, wherein: the passage comprises a cross-sectional profile, transverse relative to the longitudinal axis of the passage, defining a passage area; the channel comprises a cross-sectional profile, transverse relative to the longitudinal axis of the passage, defining a channel area; and the passage area is greater than the channel area.

Clause 8. The fluid-fitting tool of Clause 5, further comprising a third wall that extends between the first and second walls.

Clause 9. The fluid-fitting tool of any of Clauses 1 to 8, further comprising a second engagement feature spaced apart from the first engagement feature around the longitudinal axis of the passage.

Clause 10. The fluid-fitting tool of any of Clauses 1 to 9, wherein the body comprises a first arm and a second arm having an inner surface forming a cavity that is continuous with the passage, and the longitudinal axis of the passage extends through the cavity.

Clause 11. The fluid-fitting tool of Clause 10, wherein the second arm is moveable between first and second positions, wherein, in the first position, the inner surface of the first arm is positioned along the cavity to define a first cross-sectional clearance; and in the second position, at least a portion of the first arm extends into the cavity to define a second cross-sectional clearance, different from the first cross-sectional clearance, to change a cross-sectional profile of the cavity.

Clause 12. The fluid-fitting tool of Clause 11, wherein, when the second arm is in the second position, at least a portion of the second arm extends into the cavity.

Clause 13. The fluid-fitting tool of any of Clauses 1 to 12, wherein the first wall is configured to engage against the fluid fitting to rotate the fluid fitting.

Clause 14. The fluid-fitting tool of any of Clauses 1 to 13, wherein the body is configured to be slidable, along the longitudinal axis of the passage, relative to the fluid fitting while remaining rotationally fixed relative to the longitudinal axis of the passage.

Clause 15. A fluid-fitting system comprising: a fluid fitting comprising: a proximal end portion, a distal end portion; an aperture that extends between the proximal and distal ends; and a tab that extends away from an outer surface of the fluid fitting, the tab positioned adjacent the proximal end; and a fluid-fitting tool comprising: a body comprising a first end, a second end, an inner surface forming a passage that extends through the body between the first and second ends, and a first engagement feature comprising a first wall that extends from the inner surface of the passage; wherein the fluid-fitting tool comprises: a first configuration in which the fluid-fitting tool is spaced apart from the fluid fitting such that the fluid-fitting tool is rotatable relative to the fluid fitting; and a second configuration, in which at least a portion of a fluid fitting is positioned within the fluid-fitting tool such that when the body is rotated around a longitudinal axis of the passage, the first engagement feature engages against the tab such that the fluid fitting rotates with the body.

Clause 16. The fluid-fitting system of Clause 15, wherein the outer surface of the distal end portion of the fluid fitting comprises a Luer taper.

Clause 17. The fluid-fitting system of any one of Clauses 15 and 16, wherein the outer surface of the distal end portion of the fluid fitting comprises a thread.

Clause 18. The fluid-fitting system of any one of Clauses 15 to 17, further comprising a tubing coupled to the aperture of the fluid fitting and extending through the passage of the fluid-fitting tool such that the fluid-fitting tool is moveable along the tubing, relative to the fluid fitting, in a longitudinal direction.

Clause 19. The fluid-fitting system of any one of Clauses 15 to 18, wherein the body comprises a first and second arms having an inner surface forming a cavity that is continuous with the passage, and the longitudinal axis of the passage extends through the cavity.

Clause 20. The fluid-fitting system of Clause 19, wherein the second arm is moveable between first and second positions, wherein, in the first position, the inner surface of the second arm is positioned along the cavity to define a first cross-sectional clearance; and in the second position, at least a portion of the second arm extends into the cavity to define a second cross-sectional clearance, different from the first cross-sectional clearance, to change a cross-sectional profile of the cavity.

Clause 21. The fluid-fitting system of Clause 20, wherein, when the second arm is in the first position, the body is slidable along a tubing coupled to the fluid fitting, and in the second position, the second arm is engaged against the tubing to resist movement of the body relative to the tubing.

Clause 22. A method of separating a fluid fitting comprising: positioning a tubing through a passage of a fluid-fitting tool; moving the fluid-fitting tool, in a longitudinal direction along a length of the tubing, toward a fluid fitting such that a tab of the fluid fitting is at least partially positioned within the passage; and rotating the fluid-fitting tool around a longitudinal axis of the passage and relative to the fluid fitting, to engage a first wall of the fluid-fitting tool against the tab of the fluid fitting such that the fluid fitting rotates with the fluid-fitting tool.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A fluid-fitting tool comprising:
a body comprising a first end, a second end, a first arm, a second arm, an inner surface forming a passage that extends through the body between the first and second ends, and a first engagement feature comprising a first wall that extends from the inner surface of the passage and along a length that extends from the first end toward the second end of the body, the first and second arms forming a cavity that is continuous with the passage such that the longitudinal axis of the passage extends through the cavity;
wherein the passage is configured to receive at least a portion of a fluid fitting therein such that the first engagement feature engages an outer surface of the fluid fitting and rotationally couples the body and the fluid fitting such that, when the body is rotated around a longitudinal axis of the passage, the first engagement feature is configured to rotate the fluid fitting.

2. The fluid-fitting tool of claim 1, wherein the first wall extends from the first end to the second end of the body in a first direction, the passage extends from the first end to the second end of the body in a second direction, and the first and second directions are parallel relative to each other.

3. The fluid-fitting tool of claim 1, wherein the first wall extends from the inner surface in a direction away from the passage.

4. The fluid-fitting tool of claim 1, wherein the first wall extends from the inner surface in a direction toward the passage.

5. The fluid-fitting tool of claim 4, further comprising a second wall that extends from the inner surface of the passage and intersects with the first wall.

6. The fluid-fitting tool of claim 5, wherein the first and second walls form a channel of the engagement feature.

7. The fluid-fitting tool of claim 6, wherein: the passage comprises a cross-sectional profile, transverse relative to the longitudinal axis of the passage, defining a passage area; the channel comprises a cross-sectional profile, transverse relative to the longitudinal axis of the passage, defining a channel area; and the passage area is greater than the channel area.

8. The fluid-fitting tool of claim 5, further comprising a third wall that extends between the first and second walls.

9. The fluid-fitting tool of claim 1, further comprising a second engagement feature spaced apart from the first engagement feature around the longitudinal axis of the passage.

10. The fluid-fitting tool of claim 1, wherein the second arm is moveable between first and second positions, wherein, in the first position, the inner surface of the first arm is positioned along the cavity to define a first cross-sectional clearance; and in the second position, at least a portion of the first arm extends into the cavity to define a second cross-sectional clearance, different from the first cross-sectional clearance, to change a cross-sectional profile of the cavity.

11. The fluid-fitting tool of claim 1, wherein the first wall is configured to engage against the fluid fitting to rotate the fluid fitting.

12. The fluid-fitting tool of claim 1, wherein the body is configured to be slidable, along the longitudinal axis of the passage, relative to the fluid fitting while remaining rotationally fixed relative to the longitudinal axis of the passage.

13. A fluid-fitting system comprising:
a fluid fitting comprising: a proximal end portion, a distal end portion; an aperture that extends between the proximal and distal ends; and a tab that extends away from an outer surface of the fluid fitting, the tab positioned adjacent the proximal end; and
a fluid-fitting tool comprising: a body comprising a first end, a second end, a first arm, a second arm, an inner surface forming a passage that extends through the body between the first and second ends, and a first engagement feature comprising a first wall that extends from the inner surface of the passage, the first and second arms forming a cavity that is continuous with the passage such that the longitudinal axis of the passage extends through the cavity;
wherein the fluid-fitting tool comprises: a first configuration in which the fluid-fitting tool is spaced apart from the fluid fitting such that the fluid-fitting tool is rotatable relative to the fluid fitting; and a second configuration, in which at least a portion of a fluid fitting is positioned within the fluid-fitting tool such that when the body is rotated around a longitudinal axis of the passage, the first engagement feature engages against the tab such that the fluid fitting rotates with the body.

14. The fluid-fitting system of claim 13, wherein the outer surface of the distal end portion of the fluid fitting comprises a Luer taper.

15. The fluid-fitting system of claim 13, wherein the outer surface of the distal end portion of the fluid fitting comprises a thread.

16. The fluid-fitting system of claim 13, further comprising a tubing coupled to the aperture of the fluid fitting and extending through the passage of the fluid-fitting tool such that the fluid-fitting tool is moveable along the tubing, relative to the fluid fitting, in a longitudinal direction.

17. The fluid-fitting system of claim 13, wherein the second arm is moveable between first and second positions, wherein, in the first position, the inner surface of the second arm is positioned along the cavity to define a first cross-sectional clearance; and in the second position, at least a portion of the second arm extends into the cavity to define a second cross-sectional clearance, different from the first cross-sectional clearance, to change a cross-sectional profile of the cavity.

18. A method of separating a fluid fitting comprising: positioning a tubing through a passage of a fluid-fitting tool and though a cavity formed between a first arm and a second arm of the fluid fitting tool; moving the fluid-fitting tool, in a longitudinal direction along a length of the tubing, toward a fluid fitting such that a tab of the fluid fitting is at least partially positioned within the passage; and rotating the fluid-fitting tool around a longitudinal axis of the fluid fitting tool that extends through the passage and the cavity, and relative to the fluid fitting, to engage a first wall of the fluid-fitting tool against the tab of the fluid fitting such that the fluid fitting rotates with the fluid-fitting tool.

* * * * *